United States Patent [19]

Spencer

[11] Patent Number: 4,727,198

[45] Date of Patent: Feb. 23, 1988

[54] PROCESS FOR THE PRODUCTION OF FORMALDEHYDE FROM METHANE

[75] Inventor: Nicholas D. Spencer, Washington, D.C.

[73] Assignee: W. R. Grace & Co., New York, N.Y.

[21] Appl. No.: 25,043

[22] Filed: Mar. 12, 1987

[51] Int. Cl.$^4$ .............................................. C07C 45/33
[52] U.S. Cl. .................................... 568/482; 568/475
[58] Field of Search ................................. 568/475, 482

[56] References Cited

U.S. PATENT DOCUMENTS 3,996,294  12/1976  Imre et al. ...................... 260/604 R
4,607,127  8/1986  Spencer ................................ 568/482

FOREIGN PATENT DOCUMENTS 2404738  8/1975  Fed. Rep. of Germany .
58-92630  6/1983  Japan .

OTHER PUBLICATIONS

K. J. Zhen et al., J. Catalysis, 94 (1985) 501–507.

Primary Examiner—Werren B. Lone
Attorney, Agent, or Firm—Edward J. Cabic

[57] ABSTRACT

Formaldehyde is made from methane and a molecular oxygen containing gas by using a silica supported catalyst having less than 350 parts per million by weight of sodium and having a catalytically effective amount of $V_2O_5$. The low sodium form of the silica support can be made by washing silica gel or precipitated silica or by using a fumed silica. In general, the lower the sodium level, the better is the catalyst.

15 Claims, No Drawings

PROCESS FOR THE PRODUCTION OF FORMALDEHYDE FROM METHANE

BACKGROUND OF THE INVENTION

1. Field of the Invention

This invention relates to a highly selective method of producing formaldehyde, HCHO, by the partial oxidation of methane using a special type of catalyst.

2. Description of the Previously Published Art

The major commercial process to make formaldehyde is from methanol. This involves the steam reforming of methane with high grade heat to convert the methane into syn gas. The syn gas is reacted to form methanol while giving off low grade heat. Then the methanol is oxidized to formaldehyde while giving off additional low grade heat. This synthesis procedure requires multiple steps and it involves poor energy usage.

In the past a small fraction of formaldehyde was made by the partial oxidation of lower petroleum hydrocarbons which involved the partial oxidation of the hydrocarbon gas with air or oxygen under pressure, followed by rapid cooling, condensation, and absorption of the products in water to give a crude solution which must then be refined to separate formaldehyde from the other reaction products, such as methanol, acetaldehyde, propyl alcohol, propionaldehyde, and organic acids. Formaldehyde is isolated as a dilute solution, which must be concentrated to market strength. Propane and butane are the basic hydrocarbon raw materials for formaldehyde. Products manufactured by oxidation of propane and butane include formaldehyde, acetaldehyde, acetone, propionaldehyde, methanol, n-propyl alcohol, isopropyl alcohol, and butyl alcohols.

The German Offenlegungsschrift No. 2,404,738 to Bayer discloses oxidizing methane to formaldehyde by using many different types of metal oxides which may be placed on many different types of supports. The metal oxides are in Groups V, VI and/or VII of the Periodic Table. Among those listed are oxides of vanadium, niobium, tantalum, chromium, uranium, molybdenum, tungsten, manganese, technetium and rhenium, mixtures of these oxides with each other, and mixtures of these oxides with other oxides such as silica, alumina, iron oxide, calcium oxide, magnesia, sodium oxide or potassium oxide.

This reference is not helpful in finding an optimum methane conversion catalyst. It provides no attention as to the criticality of the support. It groups silica with alumina and other metal oxides yet, as was shown in U.S. Pat. No. 4,607,127, example 5, when alumina was used as a support for molybdena, it was not as effective as silica. Alumina is thought to interact with formaldehyde at high temperatures and, therefore, is also likely to be an ineffective support fo vanadium oxide.

Furthermore the Bayer reference provides no attention to the criticality of having a low sodium concentration. Sodium is present in most forms of silica that are synthesized in aqueous media because the conventional starting materials contain sodium. Offenlegungschrift No. 2404738 goes so far as to specify that up to 5 wt % Na$_2$O may be present in the working catalyst. As will be shown in Example 3, sodium in these concentrations would have a profoundly deleterious effect on selectivity to formaldehyde in the partial oxidation of methane.

U.S. Pat. No. 3,996,294 to Imre et al and assigned to Bayer discloses the use of a silica catalyst which does not contain vanadium to produce formaldehyde from methane. As will be shown in the examples, a catalyst consisting purely of silica, such as Cabosil (a product of Cabot Corporation), exhibits a lower yield of formaldehyde than is obtained with the catalyst of the present invention. Some of the examples in the Imre et al patent employ catalysts made substantially of silica along with small amounts of other metal oxides. There is no example given of using vanadium oxide, although, as in the companion German Offenlegungsschrift, there is a broad list of metal oxides which can be used, including oxides of aluminum, iron, vanadium, molybdenum, tungsten, calcium, magnesium, sodium or potassium with a specific reference that up to 5% of Na$_2$O can be used.

Japanese Patent Publication No. 58-92630 discloses a SiO$_2$-V$_2$O$_5$ catalyst, using N$_2$O as an oxidant. A similar catalyst is reported by K. J. Zhen et al in J. Catalysis, 94 (1985) 501-507. The use of N$_2$O as an oxidant is prohibitively expensive.

U.S. Pat. No. 4,607,127 to Spencer discloses a MoO$_3$-SiO$_2$ catalyst with low sodium concentration, which can be used to oxidize methane to formaldehyde using oxygen. This catalyst is less active than that of the present invention, as is shown in Comparison Example 3. The U.S. Pat. No. 4,607,127 patent makes no reference to oxides other than MoO$_3$ or SiO$_2$ as being active catalysts for this reaction.

3. Objects of the Invention

It is an object of this invention to produce formaldehyde from methane without the production of a large number of by-products so as to avoid the attendant separation problems.

It is a further object of this invention to partially oxidize methane to form formaldehyde.

It is a further object of this invention to convert methane to formaldehyde with high selectivity.

It is a further object of this invention to obtain a methane conversion catalyst for use in the present process which converts methane to formaldehyde with high selectivity.

It is a further object of this invention to produce a methane conversion catalyst having a formaldehyde yield of greater than or equal to 1% when operating at a space velocity of 5000 hr$^{-1}$ (NTP), at a temperature of 600° C. and atmospheric pressure.

These and further objects will become apparent as the description of the invention proceeds.

SUMMARY OF THE INVENTION

A catalytic process has been developed which converts methane to formaldehyde with high selectivity and activity. It employs a catalyst which is made of vanadium pentoxide, V$_2$O$_5$, supported on silicon dioxide containing low levels of sodium. The vanadium pentoxide is present in concentrations from a catalytically effective amount to 50 wt. % V, and especially preferred values are between about 0.5 wt. % and 15 wt. % V. The silica support can have a surface area in the range of 1–1000 m$^2$/g, and more preferably in the range of 30–600 m$^2$/g. The silica support should contain a low amount of sodium such as in the range of between 0 and 350 ppm Na, preferably between 0 ppm and 100 ppm Na and most preferably between 0 and 20 ppm Na or at a level of 1 ppm or less.

DESCRIPTION OF THE PREFERRED EMBODIMENT

The present invention discloses the ability to have methane converted to formaldehyde with a high yield by reacting methane simultaneously with a molecular oxygen containing gas when employing a catalyst having a catalytically effective amount of $V_2O_5$ on a silica support where the silica support is critically selected such that it has a sodium content of less than 350 ppm Na. As will be seen in the following examples, this encompasses a broad range of silica supports.

The catalyst can be prepared by either the incipient wetness technique or by evaporation to dryness of a slurry of silica in a vanadium-containing solution. In the incipient wetness technique particles of silica are impregnated by an amount of a vanadium-containing solution equal to the pore volume o the silica being impregnated. In the evaporation to dryness technique the particles of silica are placed in a volume of aqueous vanadium-containing solution and the solvent evaporated.

If the catalyst is in a powder form, it can be pelleted, crushed and screened to obtain uniform size particles for loading into the reactor. The size of the particles can be adjusted and selected depending on the geometry of the reactor.

The preferred form of vanadium for impregnation is ammonium metavanadate, which dissolves in water or in a very dilute hydrogen peroxide solution. Other possible vanadium salts would include vanadium oxalate.

The catalysts produced by either of these preferred methods have the vanadium pentoxide, $V_2O_5$, present in concentrations between a catalytically effective amount which can be as low as 0.5 wt. % and 50 wt. % V, and especially preferred values are between 0.5 wt. % and 15 wt. % V.

For the vanadium pentoxide-silica catalysts to be maximally selective for formaldehyde synthesis from methane, it appears that the silica component must possess a low sodium level. This result may be achieved by using silica with an intrinsically low sodium level such as Cabosil, a product of Cabot Corporation, or by removing sodium from a form of silica with an intrinsically high sodium level such as Intermediate Density ("ID") Silica Gel or a precipitated silica such as Sylox-15. Both of these products are made by the Davison Chemical Divison of W. R. Grace & Co. A further way to achieve the low sodium level is to use an ultrapure form of silica which has a $SiO_2$ content of at least 99.99 wt. %. This can be made, for example, by the hydrolysis of a silicon tetraalkoxide.

The silica should ultimately have a sodium content in a range of between 0 and 350 ppm Na, preferably between 0 ppm and 100 ppm Na and most preferably between 0 and 20 ppm Na or at a level of 1 ppm or less. As will be illustrated in Example 3, the presence of sodium has a profoundly deleterious effect on the HCHO selectivity of methane oxidation, when it is catalyzed by the $V_2O_5$-$SiO_2$ system. The surface area of the silica is in the range of 1-1000 $m^2/g$, preferably between 30 $m^2/g$ and 600 $m^2/g$.

The catalyst can be used to oxidize methane to formaldehyde at temperatures preferably between 400° and 700° C., a variety of pressures including atmospheric, space velocities between 500 and 100,000 $hr^{-1}$ (GHSV at NTP) and gas compositions from 0.5% $O_2$ (as oxygen or air) in $CH_4$ to the upper explosion limit which is dependent on pressure and concentration of inerts as discussed by C. M. Cooper and P. J. Wiezevich, Ind. Eng. Chem., 21, (1929) 1210. Under optimal conditions, formaldehyde selectivities in excess of 85% (carbon basis) can be obtained.

When operating at atmospheric pressure, a space velocity of 5000 $hr^{-1}$ (GHSV, NTP) and a temperature of 600° C., the catalysts made according to the present invention desirably have yields of greater than or equal to 1%.

Having described the basic aspects of our invention, the following examples are given to illustrate specific embodiments thereof.

EXAMPLE 1

This example illustrates the preparation of a catalyst using an acid washed silica gel.

A 25 g portion of dry Davison "ID" silica gel manufactured by the Davison Chemical Division of W. R. Grace & Co., which had previously been washed in dilute $H_2SO_4$ solution having a pH of 3 at 100° C. for 2 days, was screened to US 25-35 and impregnated by immersion in a solution of 0.86 g ammonium metavanadate in 40 cc water, followed by evaporation to dryness and calcination at 500° C. for 5 hours. The resulting catalyst had a vanadium loading of 1.3 wt. %, a surface area of 277 $m^2g^{-1}$ and a sodium level of 26 ppm.

EXAMPLE 2

This example illustrates the preparation of a catalyst using a fumed silica.

The catalyst was prepared by impregnating 5 g of "Cabosil", a fumed silica made by Cabot Corp., with 0.122 g ammonium metavanadate by incipient wetness, using a very dilute hydrogen peroxide solution. The impregnated product was calcined at 482° C. for 3 hours. The resulting catalyst had a vanadium loading of 1.1%, a surface area of 210 $m^2g^{-1}$ and a sodium level lower than 4 ppm. The catalyst was pressed together, crushed and screened to US 25-35.

EXAMPLE 3

This catalyst was prepared using a commercially available silica gel where the sodium content was not reduced.

A commercial grade silica gel, Davison "ID", manufactured by the Davison Chemical Division of W. R. Grace & Co., was used without further processing. A catalyst based on this material was prepared by following the method of Example 1 with the exception that the $H_2SO_4$ treatment, which lowers sodium content, was not carried out. The resulting catalyst had a vanadium loading of 1.35 wt. %, a sodium level of 520 ppm and a surface area of 270 $m^2g^{-1}$.

COMPARISON EXAMPLE 1

This catalyst was prepared according to the method described in Example 1 with the exception that the vanadium was not added to the acid washed gel. The surface area was 277 $m^2g^{-1}$ and the sodium level 26 ppm.

COMPARISON EXAMPLE 2

This catalyst consisted of "Cabosil", which had been pressed together, crushed and screened to US 25-35. The sodium level was below 4 ppm and the surface area was 210 $m^2g^{-1}$.

COMPARISON EXAMPLE 3

This catalyst consisted of 1.8 wt. % of $MoO_3$ supported on acid-washed silica gel, which was prepared as in Example 1. The method of preparation is described in U.S. Pat. No. 4,607,127, Example 11. The surface area was 277 $m^2g^{-1}$ and the sodium level was 26 ppm.

EXAMPLE 4

This example sets forth the evaluation of the catalysts made in Examples 1-3 and Comparison Examples 1-3.

A 0.20 g (approx. 0.54 cc) sample of the screened catalyst was placed on a quartz frit in a ⅜" O.D. quartz tube and covered with 0.2 g U.S. 25-35 screened quartz, which formed a preheating zone. A thermocouple was inserted into the bed such that its tip was at the entrance to the catalyst section.

Gas mixtures consisting of 90% methane and 10% oxygen were passed through the tube at 1 atm, at gas hourly space velocities of 5000 $hr^{-1}$ (NTP) while the tube was heated to 500°-650° C. The exit gases passed through heat traced Teflon ® lines to a gas chromatograph where formaldehyde and carbon dioxide were analyzed in a Poropak T column in series with a thermal conductivity detector. Other gases were analyzed using a thermal conductivity detector with a carbosphere column. The detector had been calibrated for formaldehyde against the chromatropic acid method. See West, P. W. and Sen B., Z. Anal. Chem. 153 (1956) 177-183. The results are set forth in Table 1.

TABLE 1

| | Description | Sodium/ppm | HCHO Yield at 5000 $hr^{-1}$ (GHSV, NTP) | | | | |
|---|---|---|---|---|---|---|---|
| | | | 500° C. | 575° C. | 600° C. | 625° C. | 650° C. |
| Ex. | | | | | | | |
| 1 | $V_2O_5$-AWSG | 26 | 0.12 | 1.1 | 1.4 | | |
| 2 | $V_2O_5$-Cabosil | <4 | | 0.97 | 1.0 | | |
| 3 | $V_2O_5$-Untreated SG | 520 | 0.05 | 0.33 | 0.42 | | |
| Comparison Ex. | | | | | | | |
| 1 | AWSG | 26 | | 0.14 | 0.19 | 0.4 | 0.64 |
| 2 | Cabosil | <4 | | 0.08 | 0.14 | 0.2 | 0.2 |
| 3 | $MoO_3$-AWSG | 26 | | 0.38 | 0.75 | 1.5 | 1.7 |

AWSG = acid washed silica gel

Products formed apart from formaldehyde included CO, $CO_2$ and $H_2O$. The formaldehyde yield (defined as product of formaldehyde selectivity and methane conversion) increased with temperature over the range studied.

The results show that the vanadia-silica catalysts in Examples 1 and 2 are superior catalysts with yields of greater than or equal to 1% at 600° C. and 5000 $hr^{-1}$ GHSV at NTP. The catalyst in Example 3 showed a lower formaldehyde yield than those in Example 1, showing the effect of the residual sodium in the silica gel. Pure silica in Comparison Examples 1 and 2 showed some activity as an oxidation catalyst, but a much lower formaldehyde yield than catalysts in Examples 1-3.

$MoO_3$-AWSG in Example 3, showed high yields to formaldehyde at elevated temperatures but lower yields at 600° C. than the low-sodium vanadia-silica catalysts.

In addition to showing superior yield at 600° C., the $V_2O_5$-AWSG also showed activity at temperatures of and below 500° C. This is considerably lower than the onset of activity observed for similarly-prepared $MoO_3$-AWSG catalysts such as that described in Comparison Example 3. The advantages of this activity at lower temperatures are (1) a reduction in capital costs when building the plant, since less expensive reactor materials may be employed and (2) savings in the energy needed to maintain reactor temperature.

The $V_2O_5$-AWSG catalysts also have the advantage of very low volatility, even during temperature excursions above 650° C. Under these conditions, $MoO_3$-AWSG catalysts such as those described in Comparison Example 3 are prone to lose some of their molybdenum oxide by sublimation.

It is understood that the foregoing detailed description is given merely by way of illustration and that many variations may be made therein without departing from the spirit of this invention.

What is claimed is:

1. A process to make formaldehyde from methane comprising partially oxidizing methane with a molecular oxygen containing gas over a catalyst comprising $V_2O_5$ on a silica support having a low sodium content of less than 350 ppm, said amount of $V_2O_5$ being at least a catalytically effective amount and up to an amount where the V content is about 50% by weight of the catalyst.

2. A process according to claim 1, wherein the support is a silica selected from the group consisting of silica obtained from the hydrolysis of silicon tetraalkoxides, fumed silica, acid washed silica gel, acid washed precipitated silica and mixtures thereof.

3. A process according to claim 1, wherein the silica support has a BET nitrogen surface area of at least 1 $m^2/g$.

4. A process according to claim 1, wherein the silica support has a sodium content of less than 100 ppm.

5. A process according to claim 4, wherein the silica support has a sodium content of less than 20 ppm.

6. A process according to claim 5, wherein the silica support has a sodium content of about 1 ppm or less.

7. A process according to claim 1, wherein the amount of $V_2O_5$ expressed as wt % V, is an amount up to 15 wt % V.

8. A process according to claim 7, wherein the amount of $V_2O_5$ is from about 0.5-15 wt % V.

9. A process according to claim 2, wherein the silica is a silica obtained from the hydrolysis of silicon tetraalkoxides and the sodium content is less than 4 ppm.

10. A process according to claim 9, wherein the sodium content is less than 2 ppm.

11. A process according to claim 1, wherein the silica support is an acid washed silica gel.

12. A process according to claim 1, wherein the silica support is an acid washed precipitated silica.

13. A process according to claim 1, wherein the temperature is up to 700° C.

14. A process according to claim 13, wherein the temperature is between 400° and 700° C.

15. A process according to claim 1, wherein the space velocity is 500 to 100,000 $hr^{-1}$ at normal temperature and pressure.

* * * * *